US012253681B2

(12) United States Patent
Wang

(10) Patent No.: US 12,253,681 B2
(45) Date of Patent: Mar. 18, 2025

(54) SURGICAL NAVIGATION SYSTEM, AND IMAGING METHOD OF THE SAME

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: TAIWAN MAIN ORTHOPAEDIC BIOTECHNOLOGY CO., LTD., Taichung (TW)

( * ) Notice: Subject to any disclaimer, the term of this patent is extended or adjusted under 35 U.S.C. 154(b) by 197 days.

(21) Appl. No.: 18/145,482

(22) Filed: Dec. 22, 2022

(65) Prior Publication Data

US 2023/0126207 A1 Apr. 27, 2023

Related U.S. Application Data

(63) Continuation-in-part of application No. 17/212,007, filed on Mar. 25, 2021, now abandoned.

(30) Foreign Application Priority Data

Mar. 27, 2020 (TW) ................................ 109110389

(51) Int. Cl.
*A61B 34/20* (2016.01)
*A61B 90/00* (2016.01)
(Continued)

(52) U.S. Cl.
CPC .......... *G02B 27/0176* (2013.01); *A61B 34/20* (2016.02); *A61B 90/37* (2016.02);
(Continued)

(58) Field of Classification Search
CPC ............ G02B 27/0176; G02B 27/0172; G02B 2027/014; G02B 2027/0141;
(Continued)

(56) References Cited

U.S. PATENT DOCUMENTS

| 7,753,910 B2 * | 7/2010 | Ritland .................. A61B 90/39 606/53 |
| 2006/0058604 A1 | 3/2006 | Avinash et al. |

(Continued)

FOREIGN PATENT DOCUMENTS

| CN | 108742841 A | 11/2018 |
| CN | 110638525 A | 1/2020 |

OTHER PUBLICATIONS

Search Report appended to an Office Action, which was issued to Taiwanese counterpart application No. 109110389 by the TIPO on Sep. 1, 2020, with an English translation thereof.
(Continued)

*Primary Examiner* — Hai Tao Sun
(74) *Attorney, Agent, or Firm* — Michael Best & Friedrich LLP

(57) ABSTRACT

A surgical navigation system includes a first tracking unit, a second tracking unit and a processing unit. The first tracking unit captures a first infrared image of a position identification unit that includes a reference target fixed on a patient and an instrument target disposed on a surgical instrument. The second tracking unit captures a second infrared image of the position identification unit. The processing unit performs image recognition on the first and second infrared images with respect to the position identification unit, and uses, based on a result of the image recognition, a pathological image and one of the first and second infrared images to generate an augmented reality image. When both the first and second images have both the reference target and the instrument target, one of the first image and the second image with a higher accuracy is used to generate the augmented reality image.

12 Claims, 9 Drawing Sheets

(51) Int. Cl.
*G02B 27/01* (2006.01)
*G06T 7/70* (2017.01)
*G06T 11/00* (2006.01)
*G06V 10/143* (2022.01)
*G06V 10/147* (2022.01)
*G06V 20/20* (2022.01)
*H04N 23/50* (2023.01)
*H04N 23/90* (2023.01)
*A61B 17/00* (2006.01)
*A61B 90/50* (2016.01)
*A61B 90/57* (2016.01)

(52) U.S. Cl.
CPC ............ *G02B 27/0172* (2013.01); *G06T 7/70* (2017.01); *G06T 11/00* (2013.01); *G06V 10/143* (2022.01); *G06V 10/147* (2022.01); *G06V 20/20* (2022.01); *H04N 23/50* (2023.01); *H04N 23/90* (2023.01); *A61B 2017/00486* (2013.01); *A61B 2034/2057* (2016.02); *A61B 2034/2065* (2016.02); *A61B 2034/2072* (2016.02); *A61B 2090/365* (2016.02); *A61B 2090/373* (2016.02); *A61B 2090/502* (2016.02); *A61B 2090/5025* (2016.02); *A61B 2090/571* (2016.02); *G02B 2027/0138* (2013.01); *G02B 2027/014* (2013.01); *G02B 2027/0141* (2013.01); *G02B 2027/0178* (2013.01); *G06T 2210/41* (2013.01); *G06V 2201/034* (2022.01)

(58) Field of Classification Search
CPC . G02B 2027/0178; A61B 34/20; A61B 90/37; A61B 2034/2057; A61B 2034/2065; A61B 2034/2072; A61B 2090/365; A61B 2090/373; A61B 2090/502; A61B 2090/5025; A61B 2090/571; A61B 2017/00486; G06T 7/70; G06T 11/00; G06T 2210/41; G06V 20/20; G06V 10/143; G06V 10/147; G06V 2201/034; H04N 23/50; H04N 23/90
USPC ........................................................ 345/633
See application file for complete search history.

(56) References Cited

U.S. PATENT DOCUMENTS

| | | | |
|---|---|---|---|
| 2019/0142520 A1* | 5/2019 | VanDyken | A61B 34/20 606/1 |
| 2020/0085511 A1* | 3/2020 | Oezbek | A61B 90/39 |
| 2020/0197107 A1* | 6/2020 | Ryan | A61B 90/361 |
| 2021/0132889 A1* | 5/2021 | Sato | G02B 27/0172 |

OTHER PUBLICATIONS

Search Report appended to an Office Action, which was issued to Chinese counterpart application No. 202010422466.6 by the CNIPA on Apr. 25, 2021, with an English translation thereof.

* cited by examiner

SURGICAL NAVIGATION SYSTEM, AND IMAGING METHOD OF THE SAME

CROSS-REFERENCE TO RELATED APPLICATION

This is a continuation-in-part application of U.S. patent application Ser. No. 17/212,007, filed on Mar. 25, 2021, which claims priority to Taiwanese Invention Patent Application No. 109110389, filed on Mar. 27, 2020.

FIELD

The disclosure relates to a surgical navigation system, and more particularly to a surgical navigation system that has two tracking units, and an imaging method thereof.

BACKGROUND

During a surgical operation such as orthopedic surgery or brain surgery, it is often not known whether the surgery is being performed at a precise position when the incision is small and/or the diseased portion (or surgical site) is deep.

As shown in FIG. 1, a conventional surgical navigation system 1 is adapted to provide a pathological image (not shown) to assist a medical staff 10 in operating a surgical instrument 101 to perform a surgery on a diseased portion 103 of a patient 102, and includes a reference target 11 disposed near the diseased portion 103 of the patient 102, an instrument target 12 disposed on the surgical instrument 101, an optical tracking unit 13, and a screen 14. The reference target 11 is set to a fixed position in the pathological image, and the optical tracking unit 13 is configured to photograph the diseased portion 103, to calculate a position of the instrument target 12 in an imaging coordinate system of the optical tracking unit 13 according to relative positions of the instrument target 12 and the reference target 11, and to output an augmented reality (AR) image that has the surgical instrument 101 and the pathological image of the patient 103 to the screen 14. By this, the medical staff 10 can become aware of the position of the surgical instrument 101 inside the patient's 102 body, and the distance and direction of the surgical instrument 101 relative to the diseased portion 103, thereby achieving the effect of assisting the surgery.

However, when the medical staff 10 or an assistant moves and blocks the camera of the optical tracking system 13 so any one of the reference target 11 and the instrument target 12 cannot be captured, the optical tracking system 13 will be unable to calculate the position of the surgical instrument 101, and the augmented reality image cannot be provided.

SUMMARY

Therefore, an object of the disclosure is to provide a surgical navigation system that can improve the stability or reliability of surgical navigation.

According to the disclosure, the surgical navigation system is adapted for use with a pathological image and a position identification unit to assist a medical staff in operating a surgical instrument to perform surgery on a subcutaneous diseased portion of a patient. The position identification unit includes a reference target detachably fixed on the patient, and an instrument target disposed on the surgical instrument. The surgical navigation system includes a first tracking unit, a second tracking unit and a processing unit. The first tracking unit includes a first support, a display device, and a first infrared camera device disposed on the first support. The first infrared camera device is configured to capture a first image of the position identification unit. The second tracking unit includes a second support, and a second infrared camera device disposed on the second support. The second infrared camera device is configured to capture a second image of the position identification unit. The processing unit is in signal connection with the display device, the first infrared camera device and the second infrared camera device, receives the first image and the second image respectively from the first infrared camera device and the second infrared camera device, and is configured to perform image recognition on the first image and the second image with respect to the reference target and the instrument target, to use, based on a result of the image recognition, one of the first image and the second image to generate an augmented reality image by adding a first target-related pattern that corresponds to the position identification unit into the pathological image, and to output the augmented reality image to the display device for display thereby. The processing unit is configured to, when the result of the image recognition indicates that both of the first image and the second image have both of the reference target and the instrument target, use one of the first image and the second image that has a higher accuracy to generate the augmented reality image.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
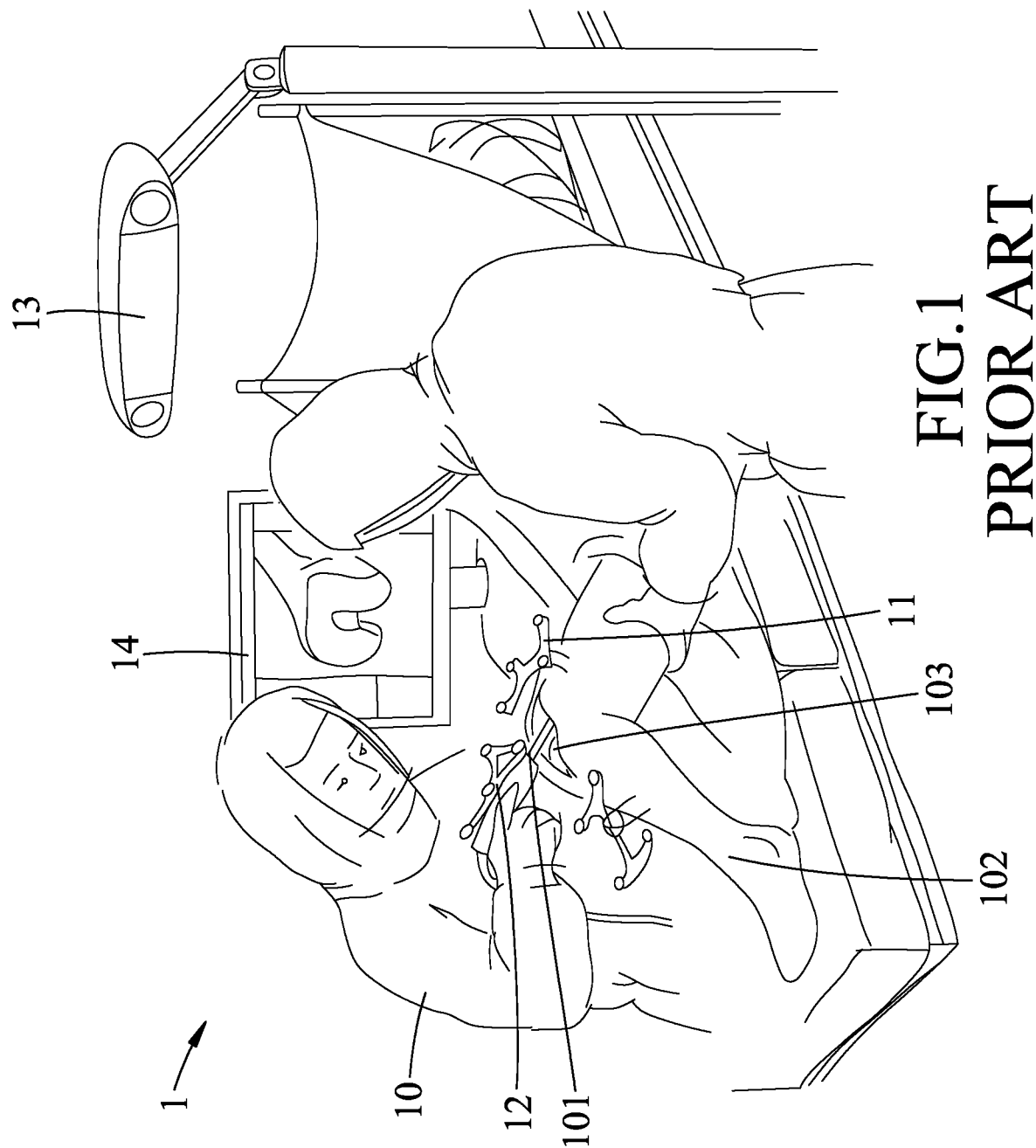
FIG. 1 is a schematic perspective view illustrating use of a conventional surgical navigation system during a surgical operation.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
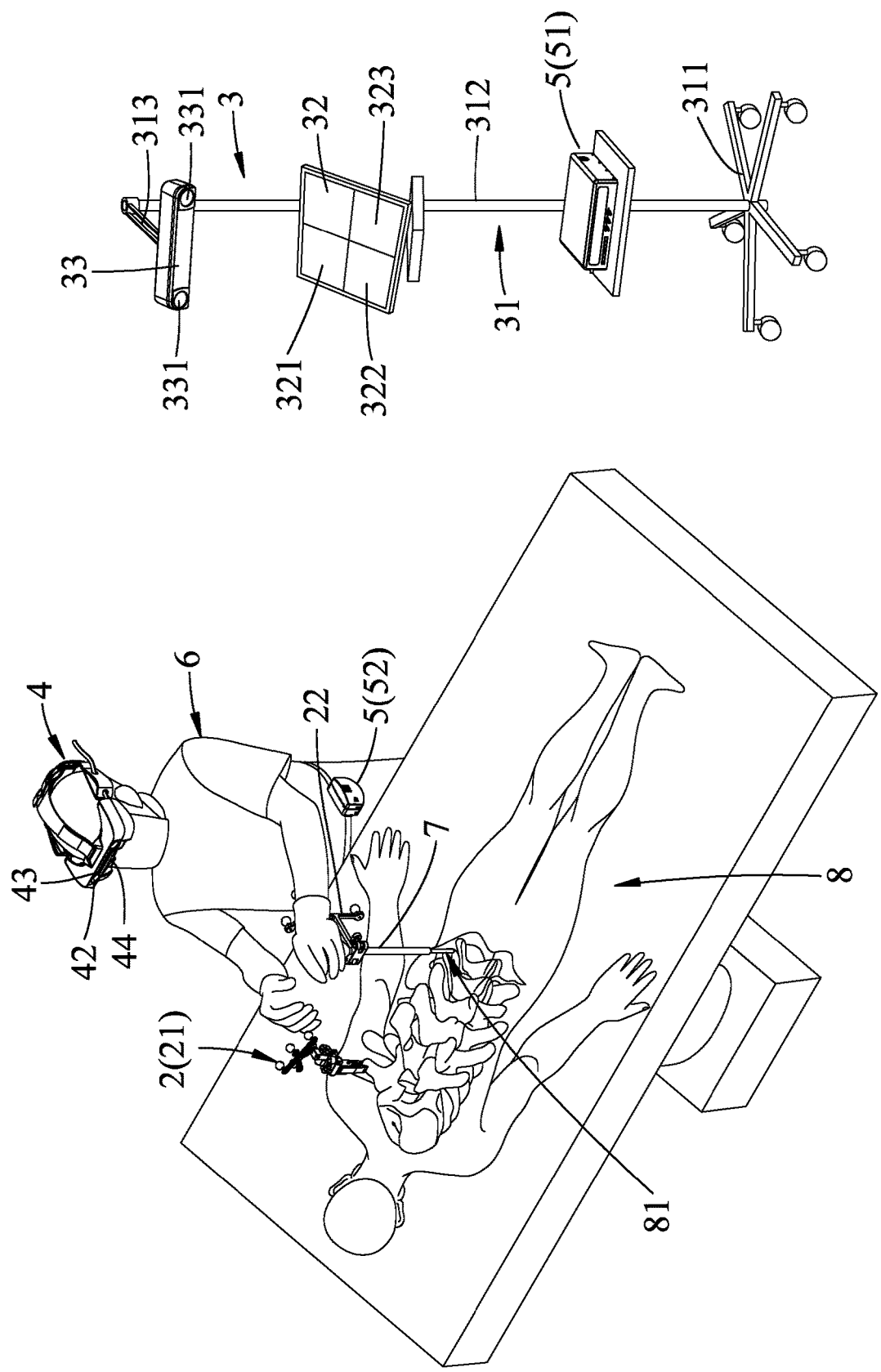
FIG. 2 is a schematic perspective view illustrating use of an embodiment of a surgical navigation system according to this disclosure during a surgical operation.

Referring to FIG. 2, an embodiment of a surgical navigation system according to this disclosure is adapted for use with a known pathological image to assist a medical staff 6 in operating a surgical instrument 7 to perform a surgery on a subcutaneous diseased portion 81 of a patient 8. The pathological image may be, but is not limited to, an image conforming with a format of digital imaging and communications in medicine (DICOM), such as an image of computed tomography (CT), an image magnetic resonance imaging (MRI), etc. The term "diseased portion" as used throughout this disclosure refers to the tissue that is to be operated on during the surgery, or simply the surgical site, regardless of whether the surgery is intended to remove the tissue or a part of the tissue, to reconnect the tissue with other tissue, to insert prosthetics or a transplant, a combination of the above, or for other purposes.

The surgical navigation system includes a position identification unit 2, a first tracking unit 3, a second tracking unit 4, and a processing unit 5.

The position identification unit 2 includes a reference target 21 to be detachably fixed on the patient 8, and an instrument target 22 disposed on the surgical instrument 7.

Figure 3:
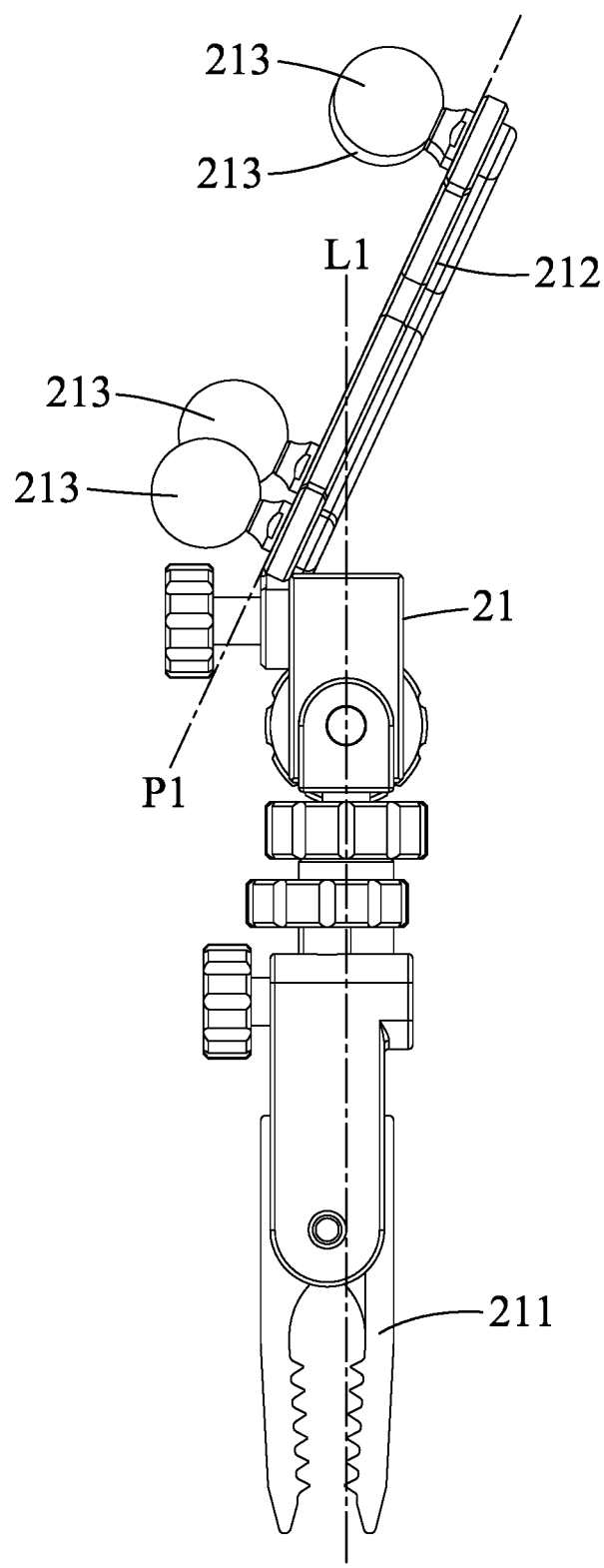
FIG. 3 is a perspective view illustrating a reference target of the embodiment.
Figure 6:
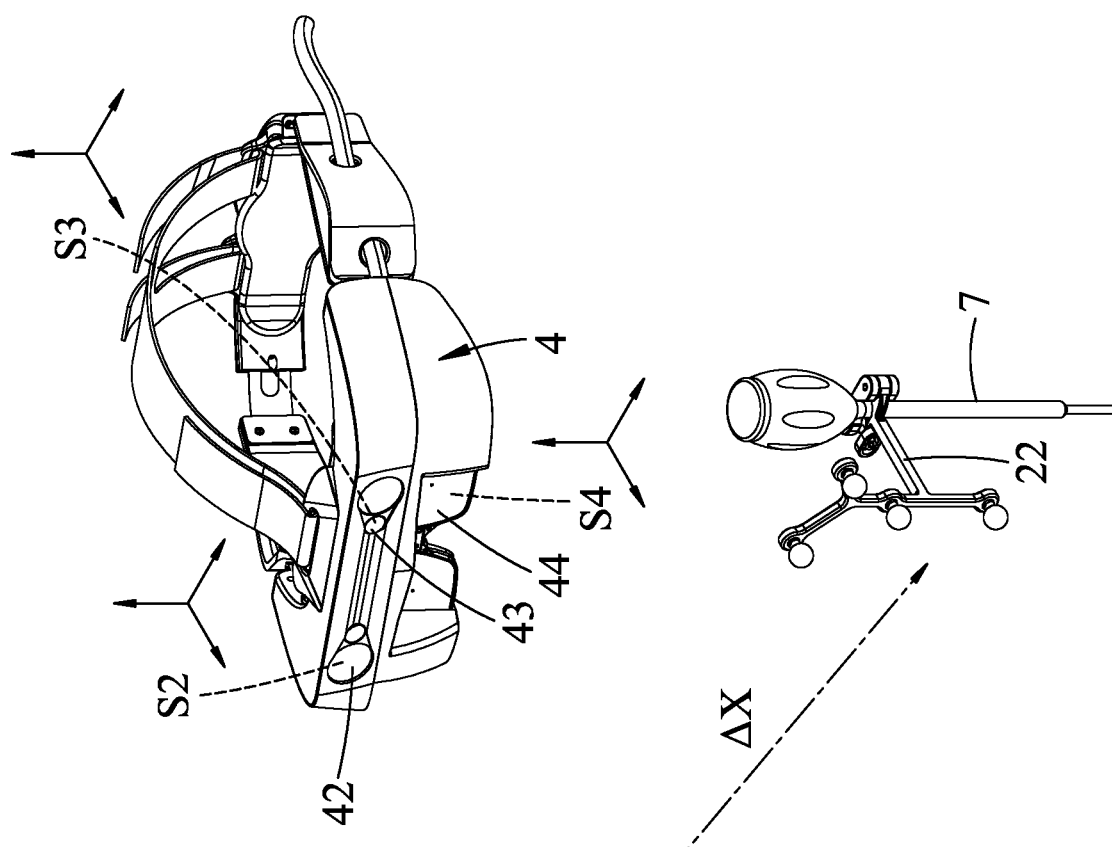
FIG. 6 is a schematic diagram illustrating coordinate systems of different components of the embodiment.
Figure 6:
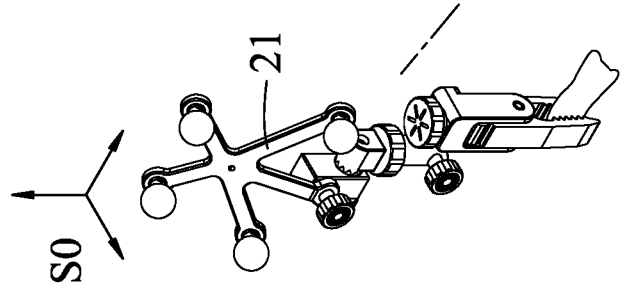
Figure 6:
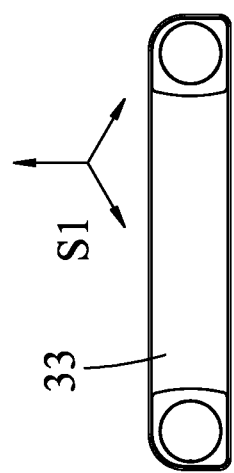

Referring to FIGS. 2, 3 and 6, the reference target 21 has a clamp 211 extending along a first axis L1 and adapted to be detachably fixed to the patient 8 through the act of clamping, a reference adapter 212 connected to the clamp 211 and having an X-shape, and four reference locator balls 213 connected to the reference adapter 212. The reference locator balls 213 are coplanar to each other and lie on a plane P1 that is nonparallel with or transverse to the first axis L1.

It is noted that the arrangement of the reference locator balls 213 of the reference target 21 and the shape of the reference adapter 212 are not limited to the above. In other modifications of the present embodiment, the reference locator balls 213 may be non-coplanar with each other, and/or the plane P1 may be parallel to the first axis L1; so long as the relative positions among the reference locator balls 213 are known.

Figure 4:
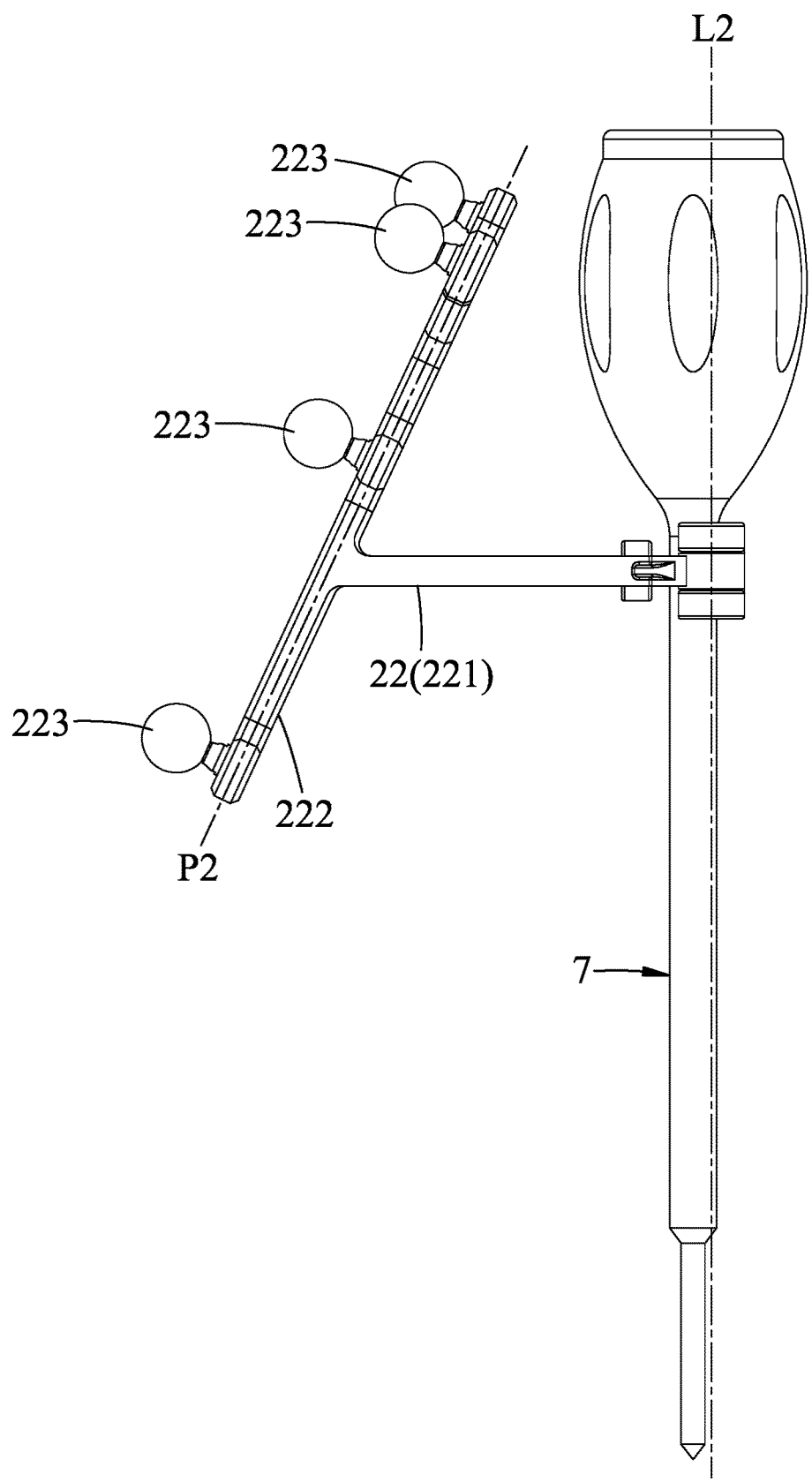
FIG. 4 is a perspective view illustrating an instrument target of the embodiment.

Referring to FIGS. 2, 4 and 6, the instrument target 22 has a fastener 221 adapted to be mounted to the surgical instrument 7 that extends along a second axis L2 so as to fasten the instrument target 22 to the surgical instrument 7, an instrument adapter 222 having a Y-shape and connected to the fastener 221, and four instrument locator balls 223 connected to the instrument adapter 222. The instrument locator balls 223 are coplanar to each other and lie on a plane P2 that is nonparallel with or transverse to the second axis L2. A geometrical arrangement of the instrument locator balls 213 of the reference target 21 is different from a geometrical arrangement of the instrument locator balls 223 of the instrument target 22. It is noted that the arrangement of the instrument locator balls 223 of the instrument target 22 and the shape of the instrument adapter 222 are not limited to the above. In other modifications of the present embodiment, the instrument locator balls 223 may be non-coplanar with each other, and the plane P2 may be parallel to the second axis L2, so long as the relative positions among the instrument locator balls 213 are known. The instrument target 22 is not limited to being one in number, and there may be two or more instrument targets 22 in other embodiments. In the present embodiment, outer surfaces of the reference locator balls 213 and the instrument locator balls 223 are made of infrared reflective material (e.g., the reference locator balls 213 and the instrument locator balls 223 have infrared reflective coatings), so as to be detected by infrared camera devices as described hereinafter. Referring to FIG. 2, the first tracking unit 3 includes a first support 31, a display device 32 disposed on the first support 31, and a first infrared camera device 33 disposed on the first support 31. The first infrared camera device 33 is disposed to face the position identification unit 2 for capturing a first image (not shown) of the position identification unit 2.

The first support 31 includes a base 311 operable in one of a movable state and a locked state, a placement frame 312 disposed on the base 311, and a balance arm 313 connected to the placement frame 312 and having the first infrared camera device 33 disposed thereon. The base 311 may include several locking caster wheels, so the base 311 is movable in the movable state where the locking caster wheels are unlocked and is fixed in position in the locked state where the locking caster wheels are locked.

The display device 32 has a pathological image area 321 for displaying the pathological image, an augmented reality (AR) area 322 for displaying an augmented reality image, and a mixed reality (MR) area 323 for displaying a mixed reality image.

It is noted that in other variations of the present embodiment, the display device 32 may be disposed to be separate from the first support 31.

In this embodiment, the pathological image area 321, the augmented reality area 322 and the mixed reality area 323 are three areas in the display device 32, and a user can arbitrarily drag, turn on or off, zoom in or out any one of these areas according to his/her own needs, so the display device 32 can present different display combinations, such as displaying images in parallel or displaying one particular image in full screen.

In the present embodiment, the first infrared camera device 33 includes two first-camera lenses 331 spaced apart from each other. The first infrared camera device 33 may be an infrared-emitting camera as an example.

Figure 5:
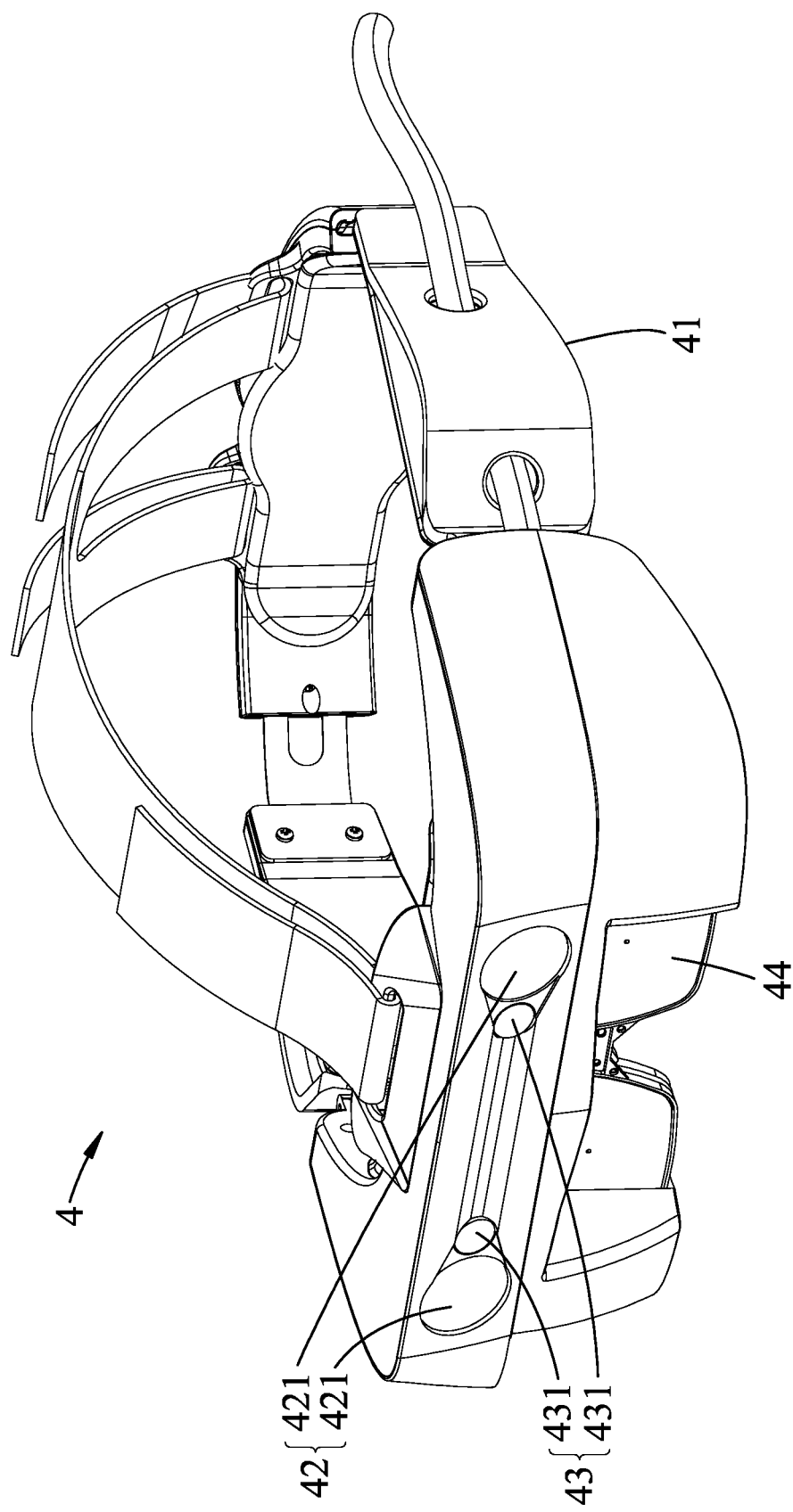
FIG. 5 is a perspective view illustrating a second tracking unit of the embodiment.

Referring to FIGS. 2 and 5, the second tracking unit 4 includes a second support 41, a second infrared camera device 42 disposed on the second support 41, a visible light camera device 43, and a display goggle 44 that includes a transparent lens so the medical staff 6 can view a scene therethrough, and is capable of displaying images on the transparent lens.

The second infrared camera device 42 is disposed to face the position identification unit 2 for capturing a second image (not shown) of the position identification unit 2 from a different angle than the first infrared camera device 41, and includes two second-camera lenses 421 spaced apart from each other. The second infrared camera device 42 may be an infrared-emitting camera as an example.

The visible light camera device 43 is disposed to face the position identification unit 2 for capturing a visible light image of the position identification unit 2, and includes two third-camera lenses 431 spaced apart from each other and disposed between the second-camera lenses 421.

In this embodiment, the second support 41 is a head-mounted device, and the second tracking unit 4 is configured such that, when the medical staff 6 wears the second support 41, the second infrared camera device 42 and the visible light camera device 43 are disposed above the eyes of the medical staff 6, and the display goggle 44 is located below the visible light camera device 43 and is in front of the eyes of the medical staff 6.

Figure 7:
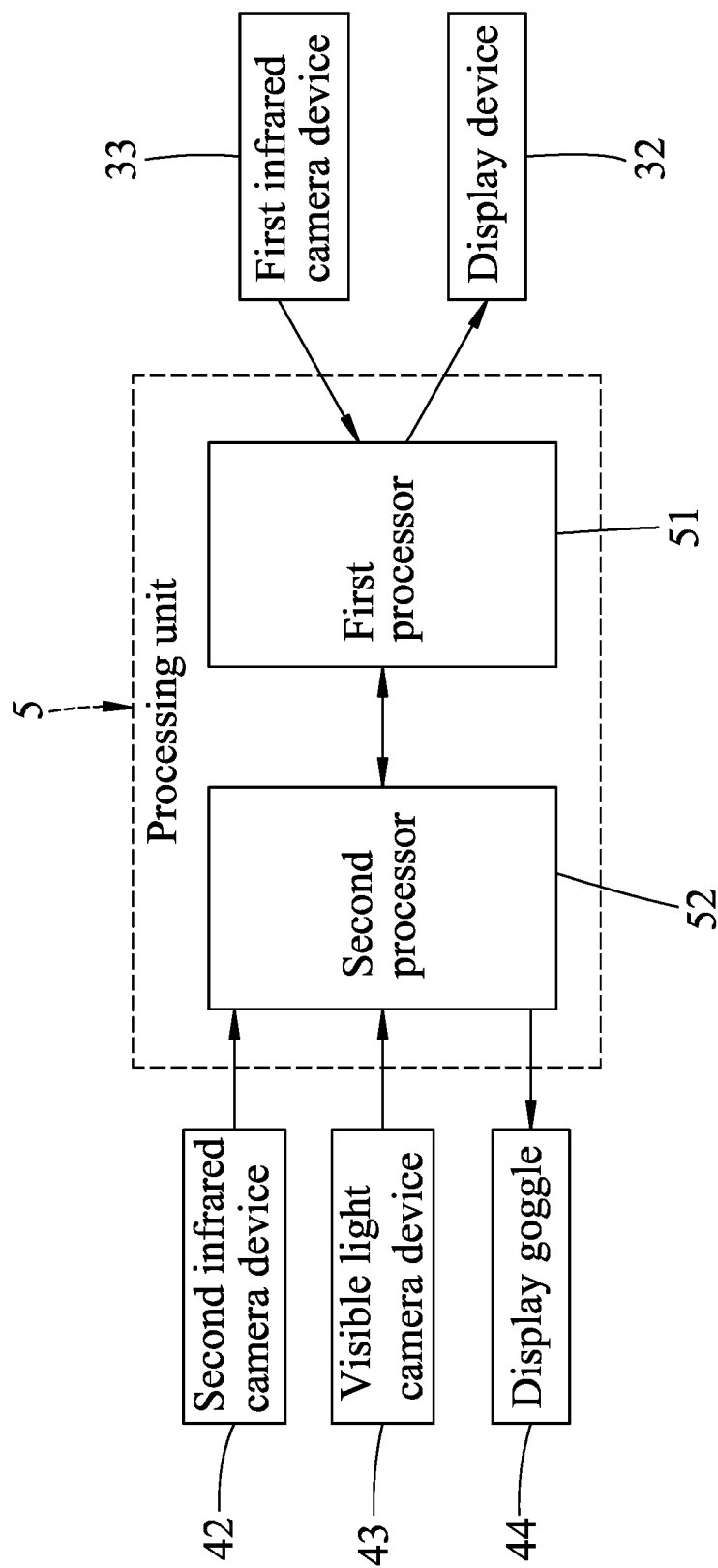
FIG. 7 is a block diagram illustrating the embodiment.

Referring to FIGS. 2 and 7, the processing unit 5 is in signal connection with the display device 32, the first infrared camera device 33, the second infrared camera device 42, the visible light camera device 43 and the display goggle 44, and is configured to receive the first image, the second image and the visible light image respectively from the first infrared camera device 33, the second infrared camera device 42 and the visible light camera device 43, and to perform image recognition on the first image and the second image with respect to the reference target 21 and the instrument target 22 (i.e., to identify the reference target 21 and the instrument target 22 from the first image and the second image).

It should be noted that the signal connection as referred in this embodiment can be realized by a wired connection (e.g., signal lines corresponding to different signal sources) or a wireless connection (e.g., wireless communication technologies such as Bluetooth and wireless network).

The processing unit 5 is configured to use, based on a result of the image recognition on the first image and the second image, one of the first image and the second image to generate an augmented reality image by adding a first target-related pattern that corresponds in position to the position identification unit 2 into the pathological image. For example, the processing unit 5 may add a pattern that represents a predetermined surgical instrument (the first target-related pattern) to the pathological image at a position that corresponds to the instrument target 22 (the position may be determined based on the reference target 21 and the instrument target 22 in said one of the first image and the second image), so as to generate the augmented reality image. Then, the processing unit 5 outputs the augmented reality image to the display device 32 for display thereby in the AR area 322 thereof. In some embodiments, the first target-related pattern may be the pattern that represents the predetermined instrument, a pattern that represents the reference target, a pattern that represents the instrument target, or a combination thereof, and this disclosure is not limited in this respect.

The processing unit 5 may further output, to the display goggle 44 based on a result of the image recognition on the second image, image data for generating a second target-related pattern that constitutes part of a mixed reality view. The image data makes the display goggle 44 display the second target-related pattern that corresponds in position to the position identification unit 2. A combination of the second target-related pattern, the pathological image and an actual view, which is the view the medical staff 6 sees through the display goggle 44, forms the mixed reality view perceived by the medical staff 6. For example, the display goggle 44 may display, based on the image data, the pathological image and a pattern that represents a predetermined surgical instrument (the second target-related pattern) at specific positions of the transparent lens thereof (the positions may be determined based on the reference target 21 and/or the instrument target 22 in the second image, and the visible light image which is similar to the actual view seen through the transparent lens), so that the medical staff 6 who wears the second support 41 may see the pathological image and the pattern that represents the predetermined surgical instrument superimposed on the actual view, thereby perceiving the mixed reality view. In some embodiments, the second target-related pattern may be the pattern that represents the predetermined instrument, the pattern that represents the reference target, the pattern that represents the instrument target, or a combination thereof, and this disclosure is not limited in this respect. In other embodiments, the display goggle 44 may display only the pathological image or only the second target-related pattern, and this disclosure is not limited in this respect.

The processing unit 5 may further generate a mixed reality image by adding, based on the result of the image recognition on the second image, the pathological image and a third target-related pattern that corresponds in position to the position identification unit 2 into the visible light image. For example, the processing unit 5 may add the pathological image and a pattern that represents a predetermined surgical instrument (the third target-related pattern) into the visible light image at specific positions (the positions may be determined based on the reference target 21 and/or the instrument target 22 in the second image), so as to generate the mixed reality image. Then, the processing unit 5 outputs the mixed reality image to the display device 32 for display thereby in the MR area 323 thereof. In some embodiments, the third target-related pattern may be the pattern that represents the predetermined instrument, the pattern that represents the reference target, the pattern that represents the instrument target, or a combination thereof, and this disclosure is not limited in this respect. In other embodiments, the processing unit 5 may add only the pathological image or only the third target-related pattern into the visible light image to form the mixed reality image, and this disclosure is not limited in this respect.

In this embodiment, the processing unit 5 includes a first processor 51 and a second processor 52. The first processor 51 is disposed on the placement frame 312 and is in signal connection with the display device 32 and the first infrared camera device 33. The second processor 52 is in signal connection with the first processor 51, the second infrared camera device 42, the visible light camera device 43 and the display goggle 44, and is adapted to be carried by the medical staff 6. In this embodiment, the second processor 52 is configured to receive the second image and the visible light image respectively from the second infrared camera device 42 and the visible light camera device 43, to transmit the second image and the visible light image to the first processor 51 for image recognition, and to perform image processing on the image data for assisting in the creation of the mixed reality view perceived by the medical staff 6. In other embodiments, the processing unit 5 may only have the first processor 51, in which case the second infrared camera device 42, the visible light camera device 43 and the display goggle 44 are in signal connection directly with the first processor 51.

Figure 8:
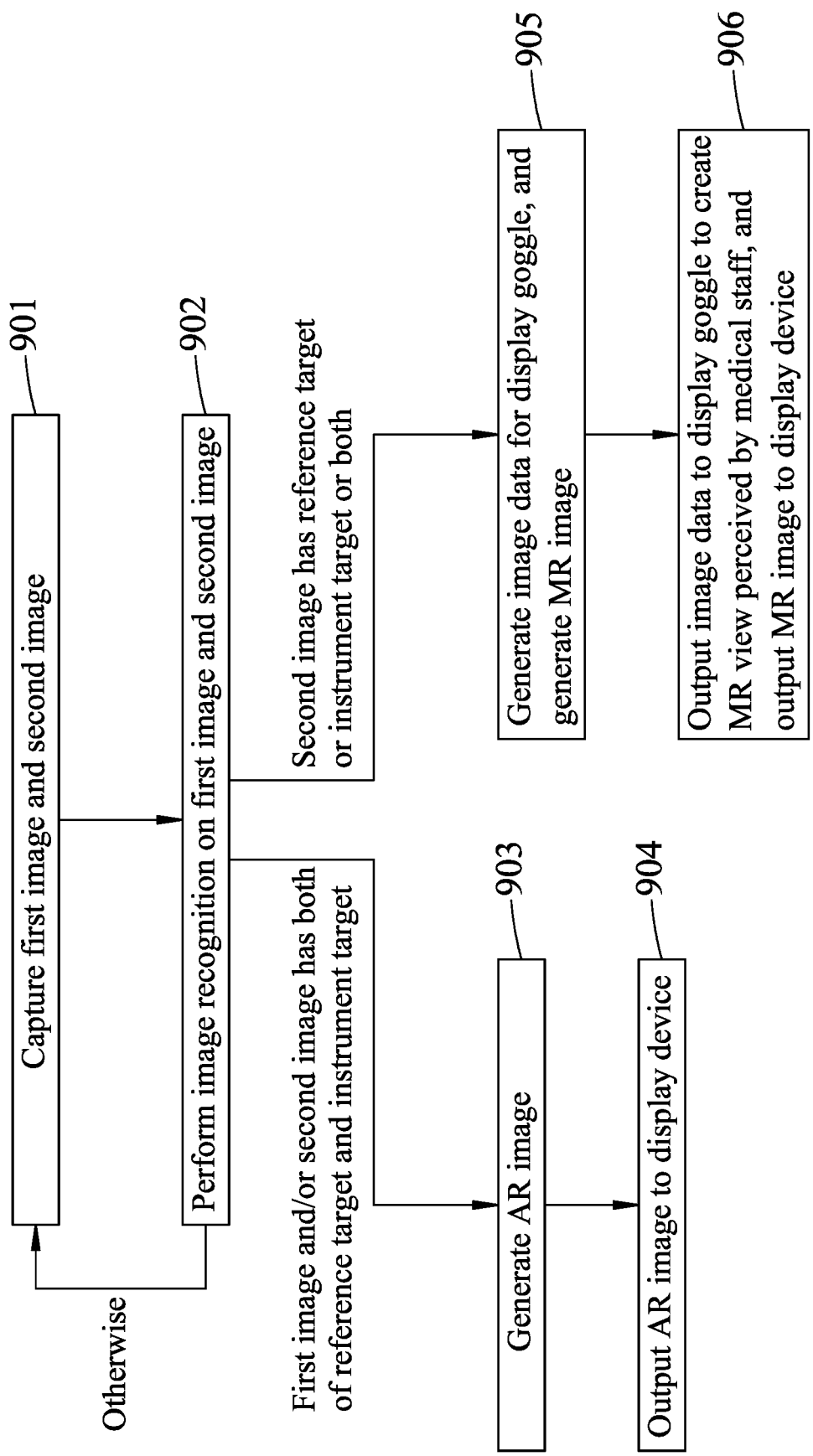
FIG. 8 is a flow chart illustrating an embodiment of an imaging method for surgical navigation according to this disclosure.

Referring to FIGS. 2 and 8, an embodiment of an imaging method for surgical navigation according to this disclosure is applied to the surgical navigation system as described above.

Before the embodiment of the imaging method is performed, the medical staff 6 may use a preoperative planning system to position the reference target 21 in the pathological image, thereby establishing a world coordinate system S0 (see FIG. 6). Since this is not a feature of this disclosure, and relevant details can be derived by a person skilled in the art according to the above description, further description is omitted herein for the sake of brevity.

In step 901, the first infrared camera device 33 captures the first image of the position identification unit 2, and the second infrared camera device 42 captures the second image of the position identification unit 2.

In step 902, the processing unit 5 performs image recognition on the first image and the second image with respect to the reference target 21 and the instrument target 22. In detail, the processing unit 5 determines whether the first image has the reference target 21, whether the first image has the instrument target 22, whether the second image has the reference target 21, and whether the second image has the instrument target 22 through image recognition techniques. The next step depends on a result of the image recognition, and is exemplified as shown in FIG. 8. When the processing unit 5 determines that one of the first and second images has both of the reference target 21 and the instrument target 22 (including a situation that both of the first and second images are determined as having both of the reference target 21 and the instrument target 22), the flow goes to step 903. When the processing unit 5 determines that the second image has one of the reference target 21 and the instrument target 22 (including a situation that the second image is determined as having both of the reference target 21 and the instrument target 22), the flow goes to step 905. It is noted that, when the second image is determined as having both of the reference target 21 and the instrument target 22, the flow goes to steps 903 and 905 at the same time. When the result of image recognition does not conform with any one of the abovementioned conditions, the flow returns to step 901. However, this disclosure is not limited to such. For example, some embodiments may only make determination on one of the abovementioned conditions (i.e., to only determine whether one of the first and second images has both of the reference target 21 and the instrument target 22, or to only determine whether the second image has one of the reference target 21 and the instrument target 22) in step 902, and the flow goes to the corresponding next step 903 or 905 when the condition is met.

In step 903, the processing unit 5 uses one of the first image and the second image to generate an augmented reality image by adding a first target-related pattern that corresponds to the position identification unit 2 into the pathological image. In detail, upon determining in step 902 that the first image has both of the reference target 21 and the instrument target 22, and that the second image does not have both of the reference target 21 and the instrument target 22, the processing unit 5 uses the first image to determine a position of the first target-related pattern in the pathological image, and generates the augmented reality image by adding the first target-related pattern into the pathological image at the position thus determined. Upon determining in step 902 that the second image has both of the reference target 21 and the instrument target 22, and that the first image does not have both of the reference target 21 and the instrument target 22, the processing unit 5 uses the second image to determine a position of the first target-related pattern in the pathological image, and generates the augmented reality image by adding the first target-related pattern into the pathological image at the position thus determined. Upon determining in step 902 that both of the first and second images have both of the reference target 21 and the instrument target 22, the processing unit 5 may select one of the first and second images which has a higher image resolution to be used in generating the augmented reality image, but this disclosure is not limited to such. In order to determine the position of the first target-related pattern in the pathological image, the processing unit 5 calculates spatial coordinates of the reference target 21 and the instrument target 22 based on the reference target 21 and the instrument target 22 in the first or second image, and adds the first target-related pattern into the pathological image based on the spatial coordinates thus calculated.

Referring to FIGS. 2, 6 and 8, the reference target 21 defines the world coordinate system S0, the first image captured by the first infrared camera device 33 is imaged on a first imaging coordinate system S1, and the second image captured by the second infrared camera device 42 is imaged on a second imaging coordinate system S2. Before the above steps are performed, the processing unit 5 may perform a calibration step to calculate intrinsic and extrinsic matrices for the first infrared camera device 33 and intrinsic and extrinsic matrices for the second infrared camera device 42, so that the processing unit 5 can perform coordinate transformation between the first imaging coordinate system S1 and the world coordinate system S0 and between the second imaging coordinate system S2 and the world coordinate system S0 through the above matrices. Accordingly, relative positions of the instrument target 22 and the reference target 21 in the first image or the second image can be used to obtain the position of the instrument target 22 in the world coordinate system S0, and the first target-related pattern can be added into the pathological image at a proper position to form the augmented reality image. The details of the coordinate transformation and the intrinsic and extrinsic matrices of the camera devices are omitted herein since one skilled in the art can deduce the details according to the above description based on known techniques.

In step 904, the processing unit 5 outputs the augmented reality image to the display device 5 for display thereby.

In step 905, in a case where the first image is determined as not having both of the reference target 21 and the instrument target 22, the processing unit 5 calculates spatial coordinates (coordinates in the world coordinate system S0) of the one of the reference target 21 and the instrument target 22 (i.e., the spatial coordinates of the reference target 21, of the instrument target 22, or of both of the reference target 21 and the instrument target 22) based on the second image, and generates, based on the spatial coordinates thus calculated, the mixed reality image and the image data which is used in the creation of the mixed reality view perceived by the medical staff 6. In a case where both of the first and second images are determined as having both of the reference target 21 and the instrument target 22, the processing unit 5 calculates spatial coordinates of both of the reference target 21 and the instrument target 22 based on either the first image or the second image, and generates, based on the spatial coordinates thus calculated, the mixed reality image and the image data that is used in the creation of the mixed reality view perceived by the medical staff 6.

Briefly, when the processing unit 5 determines that the second image has only one of the reference target 21 and the instrument target 22, a pattern that corresponds to said reference or instrument target 21, 22 will be displayed by the display goggle 44 to help create the mixed reality view perceived by the medical staff 6, and will be combined with the visible light image to form the mixed reality image to be displayed by the display device 32. When the processing unit 5 determines that the second image has both the reference target 21 and the instrument target 22, the patterns that correspond to the reference target 21 and the instrument target 22 will both be displayed by the display goggle 44 to help create the mixed reality view perceived by the medical staff 6, and will both be combined with the visible light image to form the mixed reality image to be displayed by the display device 32.

When both of the first and second images have both of the reference target 21 and the instrument target 22, the processing unit 5 may calculate spatial coordinates of the reference target 21 and the instrument target 22 in the first imaging coordinate system S1 based on the first image, and calculate spatial coordinates of the reference target 21 and the instrument target 22 in the second imaging coordinate system S2 based on the second image. Then, the processing unit 5 may transform the spatial coordinates of the reference target 21 and the instrument target 22 from the first imaging coordinate system S1 and the second imaging coordinate system S2 to the world coordinate system S0, so as to obtain a first set of spatial coordinates of the reference target 21 and the instrument target 22 in the world coordinate system S0 that corresponds to the first image, and a second set of spatial coordinates of the reference target 21 and the instrument target 22 in the world coordinate system S0 that corresponds to the second image. In practice, for each of the first set and the second set of spatial coordinates, the reference target 21 may be set at an origin (having coordinates (0, 0, 0)), while the coordinates of the instrument target 22 in the first set may differ from the coordinates of the instrument target 22 in the second set because of a difference between the first image and the second image. The processing unit 5 may select one of the first set and the second set of spatial coordinates of the reference target 21 and the instrument target 22 in the world coordinate system S0 to combine the patterns that correspond to the reference target 21 and the instrument target 22 with the actual view and/or the visible light image to form the mixed reality view and/or the mixed reality image.

The visible light image captured by the visible light camera device 43 is imaged in a third imaging coordinate system S3, and the display goggle 44 displays the second target-related pattern and/or the pathological image in a fourth imaging coordinate system S4. Since relative positions among the second infrared camera device 42, the visible light camera device 43, and the display goggle 44 are fixed, a calibration step could be performed before the steps of the embodiment to calculate intrinsic and extrinsic matrices of the visible camera device 43 and a coordinate transformation relationship among the second imaging coordinate system S2, the third imaging coordinate system S3, and the fourth imaging coordinate system S4. Accordingly, when the second image has both of the instrument target 22 and the reference target 22, the processing unit 5 can calculate the position of the instrument target 22 in the second imaging coordinate system S2 based on a relative position $\Delta X$ (e.g., a vector) that indicates relative positions of the instrument target 22 and the reference target 21 in the second image, use the extrinsic matrices of the second infrared camera device 42 to transform the position of the instrument target 22 from the second imaging coordinate system S2 to the world coordinate system S0, and calculate the position of the instrument target 22 as displayed by the display goggle 44, such that the pattern that represents the instrument target 22 and/or the second target-related pattern can be located at a proper position(s) when displayed by the display goggle 44 to create the mixed reality view perceived by the medical staff 6, and at a correct position in the visible light image to form the mixed reality image to be displayed by the display device 32. In addition, since the processing unit 5 already has the coordinate transformation relationship between the second imaging coordinate system S2 and the fourth coordinate system S4, the processing unit 5 can transform the coordinates of the reference target 21 or the instrument target 22 in the second imaging coordinate system S2 to coordinates in the fourth imaging coordinate system S4 based on the coordinate transformation relationship as long as the second infrared camera device 42 captures either the reference target 21 or the instrument target 22. That is, the processing unit 5 can form the mixed reality image without knowing the relative position $\Delta X$ that indicates relative positions of the instrument target 22 and the reference target 21 in the first image and/or second image, although the mixed reality view perceived by the medical staff 6 may not have both of the reference target 21 and the instrument target 22 in such a case.

In step 906, the processing unit 5 outputs the image data to the display goggle 44 to facilitate the creation of the mixed reality view as perceived by the medical staff 6, and outputs the mixed reality image to the display device 32 for display thereby.

In some embodiments, the processing unit 5 may output only the image data to the display goggle 44, without outputting the mixed reality image to the display device 32.

For ease of understanding, Table 1 shows a relationship between the result of the image recognition by the processing unit 5 and the resultant image types.

TABLE 1

| | | Target(s) recognized in second image | | | |
|---|---|---|---|---|---|
| | | R and I | R only | I only | No target |
| Target(s) recognized in first image | R and I | AR + MR | AR + MR | AR + MR (MR: pattern for I only) | AR only |
| | R only I only No target | | MR only (pattern for R only) | MR only (pattern for I only) | N/A |

R: reference target; I: instrument target;
$\Delta R$: augmented reality image; MR: mixed reality view/image In the case where the result of the image recognition indicates that both of the first image and the second image have both of the reference target 21 and the instrument target 22, the processing unit 5 may perform a determination as to which one of the first and second images is to be selected for subsequent use based on accuracies of the first and second images with respect to positions of a reference object (e.g., the reference target 21) in the first and second images, and use the image with a higher accuracy to generate the augmented reality image, the mixed reality view, and/or the mixed reality image.

In detail, during a surgical operation, the processing unit 5 may make a position of the reference target 21 in each of the images captured by the first-camera lenses 311 serve as an origin of coordinates (0, 0, 0) in a coordinate system (e.g., the world coordinate system S0 or the first imaging coordinate system S1), and calculate, based on the positions of the reference target 21 in the images, a first first-camera vector from the reference target 21 to one of the first-camera lenses 331, and a second first-camera vector from the reference target 21 to the other first-camera lens 331 in the coordinate system. Then, the processing unit 5 calculates a first estimated distance between the first-camera lenses 331 based on the first and second first-camera vectors in the coordinate system, and compares the first estimated distance with an actual distance between the first-camera lenses 331 that is measured in advance in the real world to obtain an accuracy of the first estimated distance that serves as the accuracy of the first image. Similarly, the processing unit 5 may make a position of the reference target 21 in each of the images captured by the second-camera lenses 421 serve as an origin of coordinates (0, 0, 0) in a coordinate system (e.g., the world coordinate system S0 or the second imaging coordinate system S2), and calculate, based on the positions of the reference target 21 in the images, a first second-camera vector from the reference target 21 to one of the second-camera lenses 421, and a second second-camera vector from the reference target 21 to the other second-camera lens 421 in the coordinate system. Then, the processing unit 5 calculates a second estimated distance between the second-camera lenses 421 based on the first and second second-camera vectors in the coordinate system, and compares the second estimated distance with an actual distance between the second-camera lenses 421 that is measured in advance in the real world to obtain an accuracy of the second estimated distance that serves as the accuracy of the second image. Then, the processing unit 5 uses one of the first and second images that has the higher accuracy to generate the augmented reality image, the mixed reality view, and/or the mixed reality image.

For example, assuming that the actual distance between the first-camera lenses 331 is 100 mm and that the actual distance between the second-camera lenses 421 is 300 mm, when the first estimated distance that is calculated based on the images captured by the first-camera lenses 331 is 99.8 mm, the accuracy of the first image would be 99.8/100=99.8%; and when the second estimated distance that is calculated based on the images captured by the second-camera lenses 421 is 299 mm, the accuracy of the second image would be 299/300=99.6%. In such a case, the processing unit 5 would use the first image to generate the augmented reality image, the mixed reality view, and/or the mixed reality image, so the augmented reality image, the mixed reality view, and/or the mixed reality image can have a better accuracy in terms of combining the target-related pattern, the pathological image, the visible light image, and/or the actual view.

In the case where the result of the image recognition indicates that the first image has both of the reference target 21 and the instrument target 22, and the second image has only the reference target 21, the processing unit 5 can calculate the position of the instrument target 22 in the world coordinate system S0 based on the relative position ΔX that indicates relative positions of the instrument target 22 and the reference target 21 in the first image. It should be noted that although no instrument target is recognized in the second image, the processing unit 5 can know a direction that the second infrared camera device 42 faces based on the reference target 21 in the second image, so the pattern that represents the instrument target 22 can still be shown for generating the mixed reality view and shown in the mixed reality image based on the relative position ΔX and the reference target 21 in the second image.

In the case where the result of the image recognition indicates that the second image has only the instrument target 22 and does not have the reference target 21, the processing unit 5 can add the pattern that represents the instrument target 22 for creating the mixed reality view and into the mixed reality image based on the coordinate transformation relationship among the second imaging coordinate system S2, the third imaging coordinate system S3 and the fourth imaging coordinate system S4. However, because no reference target is recognized in the second image, the processing unit 5 cannot know which direction the second infrared camera device 42 faces. Therefore, the processing unit 5 cannot add the pattern that represents the reference target 21 for creating the mixed reality view and into the mixed reality image even when a relative position ΔX that indicates relative positions of the reference target 21 and the instrument target 22 in the first image is known, and the mixed reality view and the mixed reality image can only have the pattern that represents the instrument target 22.

In the case where the result of the image recognition indicates that neither the first image nor the second image has both of the reference target 21 and the instrument target 22, the processing unit 5 cannot calculate the position of the instrument target 22 in the world coordinate system S0 because the relative position ΔX that indicates the relative positions of the instrument target 22 and the reference target 21 is not available. As a result, the pattern that represents the instrument target 22 cannot be combined with the pathological image to form the augmented reality image.

In this embodiment, the augmented reality image is displayed on the augmented reality area 322 of the display device 32, the mixed reality image is displayed on the mixed reality area 323 of the display device 32, and the display goggle 44 is used to provide a person wearing the second support 41 with the perception of the mixed reality view.

Figure 9:
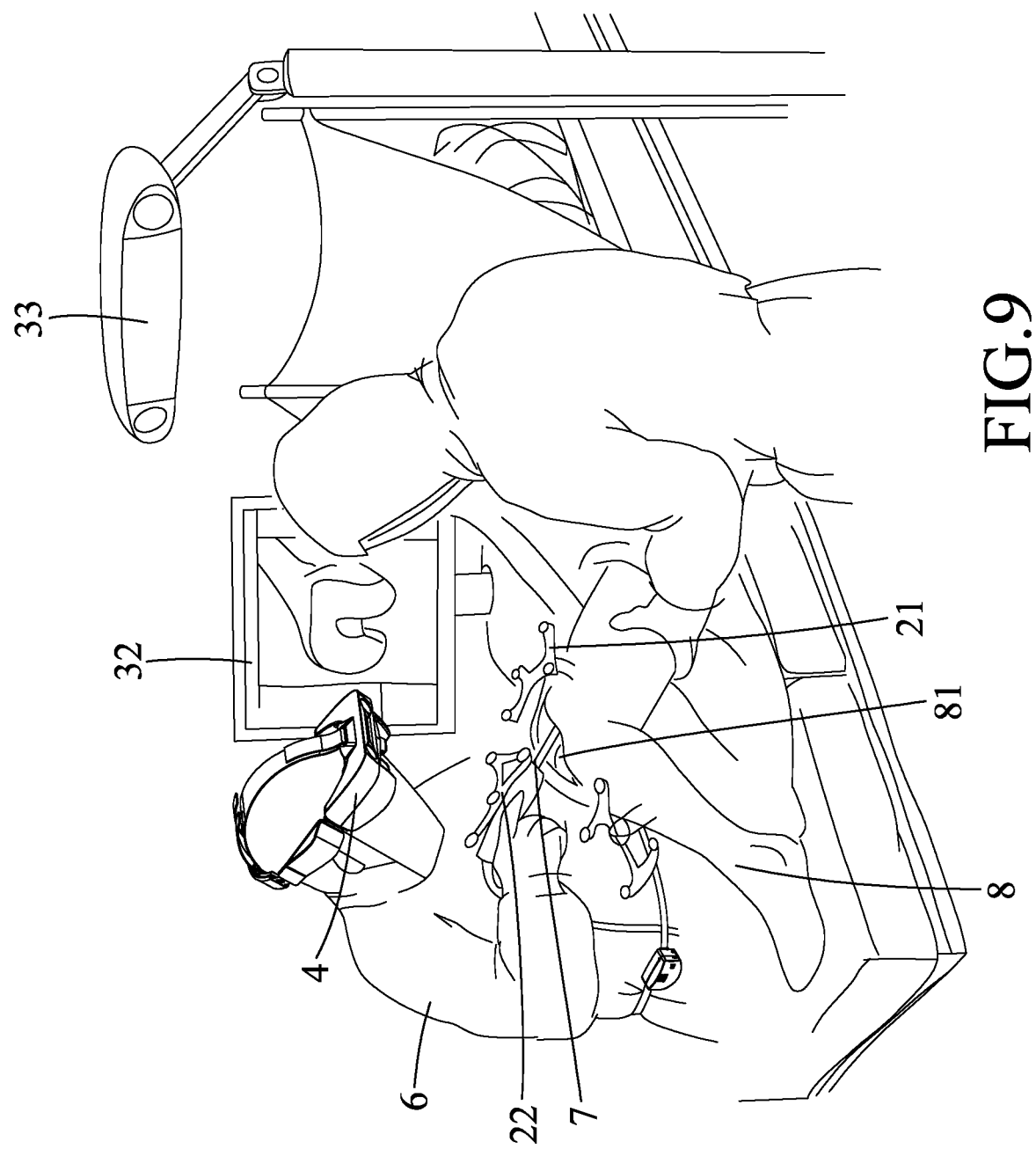
FIG. 9 is a schematic diagram illustrating that the embodiments according to this disclosure are also applicable to a knee surgery.

It is noted that the embodiment of the surgical navigation system according to this disclosure is applicable to various types of surgery operations, such as spine surgery (see FIG. 2), knee surgery (see FIG. 9), etc.

The advantages of the foregoing embodiment can be summarized as follows:

1. By providing the second infrared camera device 42 of the second tracking unit 4 to capture the second image of the subcutaneous diseased portion 81, when the first infrared camera device 33 of the first tracking system 3 cannot capture one or both of the reference target 21 and the instrument target 22, that is, the first image does not have the reference target 21 and/or the instrument target 22, the processing unit 5 can still use the second image and the pathological image to form the augmented reality image, and output the augmented reality image to the display device 32, so as to reduce the chance that a navigation image (the augmented reality image) cannot be shown because a line of vision between the first infrared camera device 33 and the subcutaneous diseased portion 81 is blocked, thereby achieving the effect of improving the stability or reliability of surgical navigation.

2. Because of safety reasons, there are few situations that the sight of the medical staff 6 would be blocked by external objects, so the second infrared camera device 42 and the visible light camera device 43 that are disposed above the eyes of the medical staff 6 would hardly ever be blocked during a surgical operation, thereby achieving the effect of improving the stability or reliability of the surgical navigation. 3. The processing unit 5 can use the second image to help create the mixed reality view perceived by the medical staff 6 where the medical staff can see the pathological image and the third target-related pattern via the display goggle 44, so the medical staff 6 can focus on the subcutaneous diseased portion 81 of the patient 8 without continuously having to look up at the display device 32, thereby achieving the effect of improving the convenience of the operation.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A surgical navigation system adapted for use with a pathological image and a position identification unit to assist a medical staff in operating a surgical instrument to perform surgery on a subcutaneous diseased portion of a patient, the position identification unit including a reference target detachably fixed on the patient, and an instrument target disposed on the surgical instrument, said surgical navigation system comprising:
   a first tracking unit including a first support, a display device, and a first infrared camera device disposed on said first support, wherein said first infrared camera device is configured to capture a first image of the position identification unit;
   a second tracking unit including a second support, and a second infrared camera device disposed on said second support, wherein said second infrared camera device is configured to capture a second image of the position identification unit; and
   a processing unit in signal connection with said display device, said first infrared camera device and said second infrared camera device, receiving the first image and the second image respectively from said first infrared camera device and said second infrared camera device, and configured to perform image recognition on the first image and the second image with respect to the reference target and the instrument target, to use, based on a result of the image recognition, one of the first image and the second image to generate an augmented reality image by adding a first target-related pattern that corresponds to the position identification unit into the pathological image, and to output the augmented reality image to said display device for display thereby,
   wherein said processing unit is configured to, when the result of the image recognition indicates that both of the first image and the second image have both of the reference target and the instrument target, use one of the first image and the second image that has a higher accuracy to generate the augmented reality image;
   wherein said first infrared camera device includes two first-camera lenses that are spaced apart from each other, and said second infrared camera device includes two second-camera lenses that are spaced apart from each other;
   wherein said processing unit is configured to, when the result of the image recognition indicates that both of the first image and the second image have both of the reference target and the instrument target, calculate a first first-camera vector and a second first-camera vector based on images captured by said first-camera lenses, and calculate a first second-camera vector and a second second-camera vector based on images captured by said second-camera lenses, wherein the first and second first-camera vectors are vectors from the reference target to said first-camera lenses, respectively, and the first and second second-camera vectors are vectors from the reference target to said second-camera lenses, respectively;
   wherein said processing unit is configured to calculate a first estimated distance between said first-camera lenses based on the first and second first-camera vectors, and a second estimated distance between said second-camera lenses based on the first and second second-camera vectors; and
   wherein said processing unit is configured to determine an accuracy of the first image based on an accuracy of the first estimated distance, and an accuracy of the second image based on an accuracy of the second estimated distance.

2. The surgical navigation system of claim 1, wherein said second tracking unit further includes a display goggle disposed on said second support and to be worn by the medical staff, and said processing unit is in signal connection with said display goggle, and is further configured to output, based on one of the first image and the second image, image data for generating a second target-related pattern that constitutes part of a mixed reality view to said display goggle, wherein the image data makes said display goggle display the second target-related pattern that corresponds to the position identification unit, and wherein a combination of the second target-related pattern and an actual view, which the medical staff sees through said display goggle, forms the mixed reality view perceived by the medical staff; and
   wherein said processing unit is configured to, when the result of the image recognition indicates that both of the first image and the second image have both of the reference target and the instrument target, use one of the first image and the second image that has the higher accuracy to output the image data for generating the second target-related pattern.

3. The surgical navigation system of claim 2, wherein said second tracking unit further includes a visible light camera device for capturing a visible light image of the position identification unit;
   wherein said processing unit is in signal connection with said visible light camera device, receives the visible light image from said visible light camera device, and is further configured to generate a mixed reality image by adding, based on one of the first image and the second image, a third target-related pattern that corresponds to the position identification unit into the visible light image, and to output the mixed reality image to said display device for display thereby; and
   wherein said processing unit is configured to, when the result of the image recognition indicates that both of the first image and the second image have both of the reference target and the instrument target, generate the mixed reality image by adding, based on one of the first image and the second image that has the higher accuracy, the third target-related pattern into the visible light image.

4. The surgical navigation system of claim 3, wherein said second infrared camera device includes two lenses spaced apart from each other, and said visible light camera device includes two lenses spaced apart from each other and positioned between said lenses of said second infrared camera device.

5. The surgical navigation system of claim 4, wherein said second support is a head-mounted device, said second infrared camera device and said visible light camera device are disposed above eyes of the medical staff when the medical staff wears said second support, and said display goggle is disposed below said visible light camera device and in front of the eyes of the medical staff when the medical staff wears said second support.

6. The surgical navigation system of claim 3, wherein said display device is disposed on said first support, and has a pathological image area for displaying the pathological image, an augmented reality area for displaying the augmented reality image, and a mixed reality area for displaying the mixed reality image.

7. The surgical navigation system of claim 1, wherein said first support includes a base, a placement frame disposed on said base, and a balance arm connected to said placement frame and having said first infrared camera device disposed thereon; and
  wherein said base is configured to switch between a movable state where said base is movable, and a locked state where said base is fixed in position.

8. The surgical navigation system of claim 7, wherein said processing unit includes a first processor and a second processor, said first processor being disposed on said placement frame and in signal connection with said display device and said first infrared camera device, said second processor being in signal connection with said first processor and said second infrared camera device and is adapted to be carried by the medical staff.

9. The surgical navigation system of claim 1, wherein, through performing the image recognition, said processing unit determines whether the first image has the reference target, whether the first image has the instrument target, whether the second image has the reference target, and whether the second image has the instrument target;
  wherein, upon determining that the first image has both of the reference target and the instrument target, and that the second image does not have both of the reference target and the instrument target, said processing unit uses the first image to determine a position of the first target-related pattern in the pathological image, generates the augmented reality image by adding the first target-related pattern into the pathological image at the position thus determined, and outputs the augmented reality image to said display device for display thereby; and
  wherein, upon determining that the second image has both of the reference target and the instrument target, and that the first image does not have both of the reference target and the instrument target, said processing unit uses the second image to determine a position of the first target-related pattern in the pathological image, generates the augmented reality image by adding the first target-related pattern into the pathological image at the position thus determined, and outputs the augmented reality image to said display device for display thereby.

10. A surgical navigation system adapted for use with a pathological image to assist a medical staff in operating a surgical instrument to perform surgery on a subcutaneous diseased portion of a patient, said surgical navigation system comprising:
  a position identification unit including a reference target detachably fixed on the patient, and an instrument target disposed on the surgical instrument;
  a first tracking unit including a first support, a display device, and a first infrared camera device disposed on said first support, wherein said first infrared camera device is configured to capture a first image of said position identification unit;
  a second tracking unit including a second support, and a second infrared camera device disposed on said second support, wherein said second infrared camera device is configured to capture a second image of said position identification unit; and
  a processing unit in signal connection with said display device, said first infrared camera device and said second infrared camera device, receiving the first image and the second image respectively from said first infrared camera device and said second infrared camera device, and configured to perform image recognition on the first image and the second image with respect to said reference target and said instrument target, to use, based on a result of the image recognition, one of the first image and the second image to generate an augmented reality image by adding a first target-related pattern that corresponds to said position identification unit into the pathological image, and to output the augmented reality image to said display device for display thereby,
  wherein said processing unit is configured to, when the result of the image recognition indicates that both of the first image and the second image have both of said reference target and said instrument target, use one of the first image and the second image that has a higher accuracy to generate the augmented reality image;
  wherein said first infrared camera device includes two first-camera lenses that are spaced apart from each other, and said second infrared camera device includes two second-camera lenses that are spaced apart from each other;
  wherein said processing unit is configured to, when the result of the image recognition indicates that both of the first image and the second image have both of said reference target and said instrument target, calculate a first first-camera vector and a second first-camera vector based on images captured by said first-camera lenses, and calculate a first second-camera vector and a second second-camera vector based on images captured by said second-camera lenses, wherein the first and second first-camera vectors are vectors from said reference target to said first-camera lenses, respectively, and the first and second second-camera vectors are vectors from said reference target to said second-camera lenses, respectively;
  wherein said processing unit is configured to calculate a first estimated distance between said first-camera lenses based on the first and second first-camera vectors, and a second estimated distance between said second-camera lenses based on the first and second second-camera vectors; and
  wherein said processing unit is configured to determine an accuracy of the first image based on an accuracy of the first estimated distance, and an accuracy of the second image based on an accuracy of the second estimated distance.

11. The surgical navigation system of claim 10, wherein said reference target has a clamp, a reference adapter and four reference locator balls, said clamp extending along an axis and being configured to be detachably fixed on the patient, said reference adapter being connected to said clamp, said four reference locator balls being connected to said reference adapter, being coplanar to each other, and lying on a plane that is nonparallel to the axis along which said clamp extends.

12. The surgical navigation system of claim 10, wherein said instrument target has a fastener adapted to be mounted to the surgical instrument which extends along an axis, an instrument adapter connected to said fastener, and four instrument locator balls connected to said instrument adapter, being coplanar to each other, and lying on a plane that is nonparallel to the axis along which the surgical instrument extends.

* * * * *